US009002088B2

(12) United States Patent
Ferguson

(10) Patent No.: US 9,002,088 B2
(45) Date of Patent: Apr. 7, 2015

(54) METHOD AND APPARATUS FOR CREATING NONDESTRUCTIVE INSPECTION POROSITY STANDARDS

(75) Inventor: Kathy L. Ferguson, Woodinville, WA (US)

(73) Assignee: The Boeing Company, Chicago, IL (US)

( * ) Notice: Subject to any disclaimer, the term of this patent is extended or adjusted under 35 U.S.C. 154(b) by 207 days.

(21) Appl. No.: 13/606,754

(22) Filed: Sep. 7, 2012

(65) Prior Publication Data

US 2014/0072197 A1 Mar. 13, 2014

(51) Int. Cl.
*G06K 9/00* (2006.01)
*G01N 15/08* (2006.01)

(52) U.S. Cl.
CPC .................................. *G01N 15/088* (2013.01)

(58) Field of Classification Search
None
See application file for complete search history.

(56) References Cited

U.S. PATENT DOCUMENTS

2008/0148854 A1* 6/2008 Georgeson et al. ............. 73/599
2010/0278440 A1* 11/2010 Dragovich et al. ........... 382/218

OTHER PUBLICATIONS

"Ultrasonic Inspection," Section 7, In: Acceptable Methods, Techniques, and Practices—Aircraft Inspection and Repair, Advisory Circular AC43.13-1B, Department of Transportation, Federal Aviation Administration, Sep. 8, 1998, 15 Pages.

* cited by examiner

*Primary Examiner* — Bhavesh Mehta
*Assistant Examiner* — Siamak Harandi
(74) *Attorney, Agent, or Firm* — Yee & Associates, P.C.

(57) ABSTRACT

A method and apparatus for establishing nondestructive inspection porosity standards. In one illustrative embodiment, a plurality of samples is formed using a different technique for each sample in the plurality of samples such that each sample in the plurality of samples has a different porosity from other samples in the plurality of samples. Each sample in the plurality of samples has a same set of selected properties as a selected part type. A porosity level is identified for each sample using volumetric data extracted from a three-dimensional image for each sample generated using a computed tomography system. A group of standards is established for a group of selected porosity levels from the plurality of samples based on the porosity level identified for each sample in the plurality of samples. The group of standards is configured for use in performing nondestructive inspection of a part of the selected part type.

18 Claims, 6 Drawing Sheets

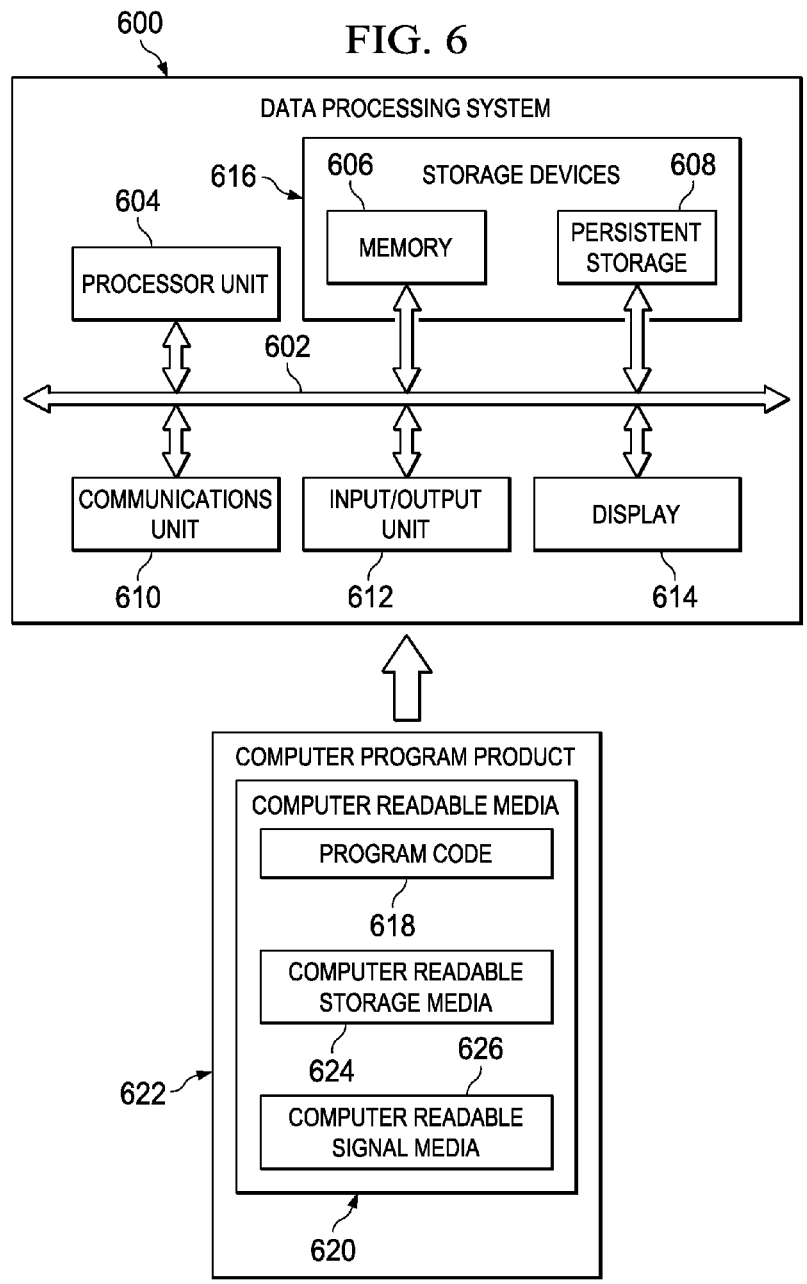

METHOD AND APPARATUS FOR CREATING NONDESTRUCTIVE INSPECTION POROSITY STANDARDS

BACKGROUND INFORMATION

1. Field:

The present disclosure relates generally to nondestructive inspection (NDI) standards and, in particular, to nondestructive inspection standards for porosity. Still more particularly, the present disclosure relates to a method and apparatus for creating nondestructive inspection standards for porosity using computed tomography (CT).

2. Background:

Nondestructive inspection (NDI) refers to the group of analysis techniques that are used to evaluate the properties of an object without altering the object. Nondestructive inspection may also be referred to as nondestructive examination (NDE), nondestructive testing (NDT), or nondestructive evaluation (NDE). Different types of nondestructive inspection techniques may be used to evaluate composite materials and objects comprised of composite materials. These different techniques include, but are not limited to, ultrasonic testing (UT), radiographic testing, and vibration analysis.

Oftentimes, standards are created for use in evaluating an object using nondestructive inspection. As used herein, a "standard" is a reference article or sample of material having a set of properties that are the same as the object being evaluated. These properties may include, for example, without limitation, material composition, geometry, thickness, and/or other types of properties.

In some cases, standards are used to calibrate the nondestructive inspection system used to test an object. Additionally, standards may be inspected using the nondestructive inspection system that is used to test the object. Data generated by the nondestructive inspection system for these standards may be used as reference data for comparison with part data generated by the nondestructive inspection system for the part. In other words, the reference data may be used for comparison when evaluating the part data.

As one illustrative example, a group of standards may be established for evaluating the porosity of a part comprised of composite material. In this example, each standard in the group of standards is a sample of composite material that has been previously identified as having a particular porosity.

However, with some currently available methods for establishing nondestructive inspection standards, the time, effort, and/or cost required to form samples of composite material and identify the porosity for each of these samples may be greater than desired. For example, with some currently available methods, forming a sample may require performing any number of sanding operations, polishing operations, cutting operations, and/or other types of operations to prepare at least one edge of the sample for testing. These operations may be more time-consuming than desired.

Further, the sample may then be analyzed using, for example, without limitation, ultrasound testing techniques. Software may then be used to estimate a level of porosity for an edge of the sample based on a height and weight of the sample. This estimated porosity may then be used to estimate a level of porosity for the entire sample. However, this type of estimation may be less accurate than desired.

Consequently, the standards established using these types of currently available methods may not allow the object for which the standards were established to be evaluated as well as desired. Therefore, it would be desirable to have a method and apparatus that takes into account at least some of the issues discussed above, as well as other possible issues.

SUMMARY

In one illustrative embodiment, a method for establishing nondestructive inspection standards is present. A plurality of samples is formed using a different technique for each sample in the plurality of samples such that each sample in the plurality of samples has a different porosity from a number of other samples in the plurality of samples. Each sample in the plurality of samples has a same set of selected properties as a selected part type. A porosity level is identified for each sample in the plurality of samples using volumetric data extracted from a three-dimensional image for each sample generated using a computed tomography system. A group of standards is established for a group of selected porosity levels from the plurality of samples based on the porosity level identified for each sample in the plurality of samples. The group of standards is configured for use in performing nondestructive inspection of a part of the selected part type.

In another illustrative embodiment, a method for evaluating a part using a nondestructive inspection system is present. Reference inspection data is generated for a group of standards by performing nondestructive inspection of each standard in the group of standards for the part using the nondestructive inspection system. The group of standards is established from a plurality of samples based on a porosity level identified for each sample in the plurality of samples using volumetric data extracted from a three-dimensional image for each sample generated using a computed tomography system. Part inspection data is generated for the part by performing the nondestructive inspection of the part using the nondestructive inspection system. A part's porosity level is identified for the part using the reference inspection data and the part inspection data.

In yet another illustrative embodiment, an apparatus comprises a plurality of samples and a data analyzer. The plurality of samples is formed such that each sample in the plurality of samples has a different porosity from a number of other samples in the plurality of samples and such that each sample in the plurality of samples has a same set of selected properties as a selected part type. The data analyzer is configured to identify a porosity level for each sample in the plurality of samples using volumetric data extracted from a three-dimensional image for each sample generated using a computed tomography system. A group of standards for a group of selected porosity levels is established from the plurality of samples based on the porosity level identified for each sample in the plurality of samples. The group of standards is configured for use in performing nondestructive inspection of a part of the selected part type.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 6 is an illustration of a data processing system in the form of a block diagram in accordance with an illustrative embodiment.

DETAILED DESCRIPTION

The different illustrative embodiments recognize and take into account different types of considerations. For example, the different illustrative embodiments recognize and take into account that it may be desirable to have a method and apparatus for establishing nondestructive inspection standards for porosity more quickly, more easily, and more accurately than is possible with some currently available methods for establishing these types of standards.

Further, the illustrative embodiments recognize and take into account that it may be desirable to have a method and apparatus for establishing nondestructive inspection standards that are less expensive than some currently available methods for establishing these standards. For example, the illustrative embodiments recognize and take into account that reducing the size of the samples of composite material needed for establishing standards may reduce the expense associated with establishing these standards. Additionally, reducing the overall time needed to form the samples and to identify the porosity for each of these samples may reduce the expense associated with establishing the standards.

Thus, the different illustrative embodiments provide a method and apparatus for establishing nondestructive inspection standards. In particular, a method and apparatus are provided for establishing a group of standards for use in evaluating the porosity of any part of a selected part type using a nondestructive inspection system.

Figure 1:
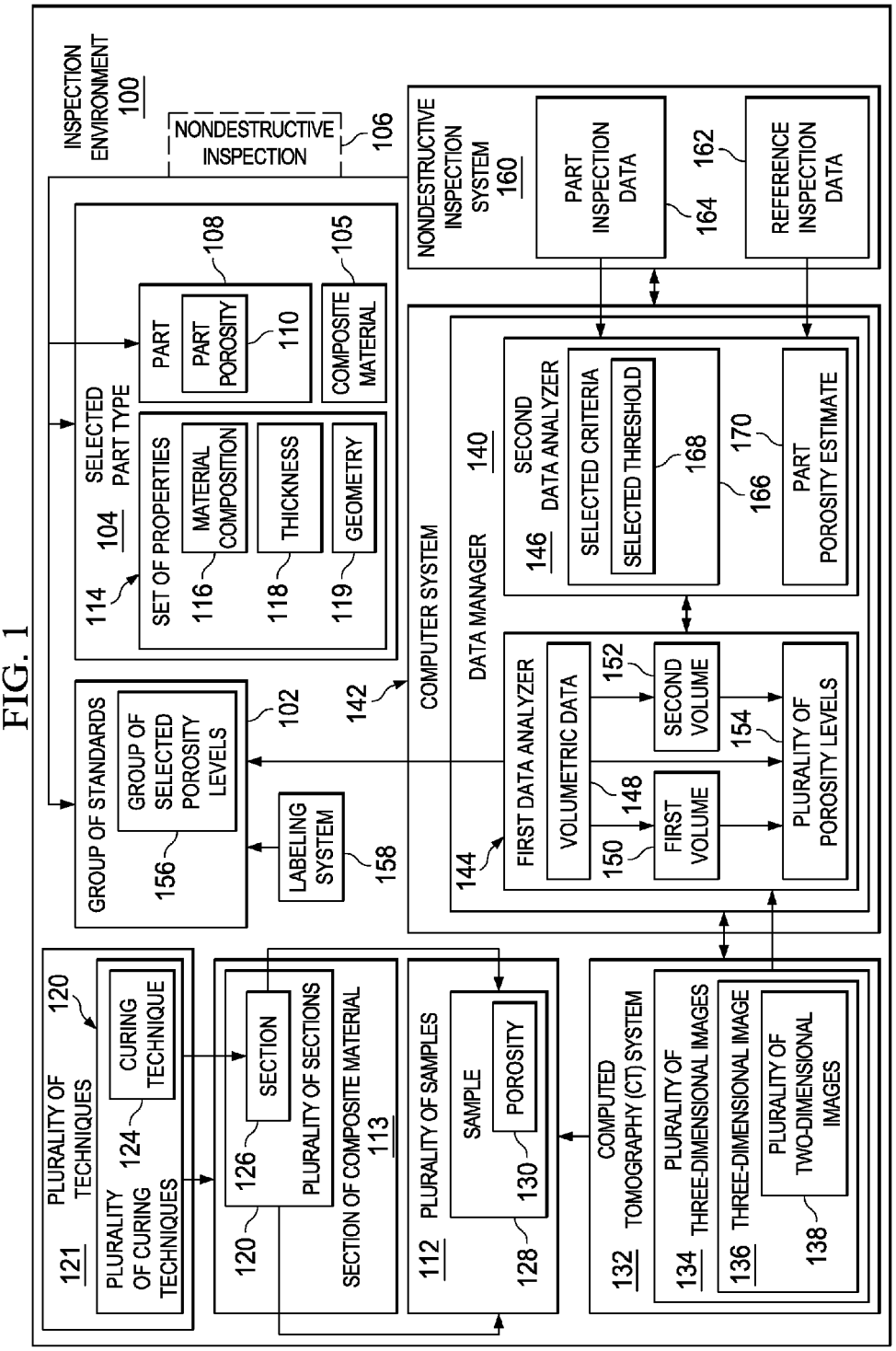
FIG. 1 is an illustration of an inspection environment in the form of a block diagram in accordance with an illustrative embodiment.

With reference now to FIG. 1, an illustration of an inspection environment in the form of a block diagram is depicted in accordance with an illustrative embodiment. In FIG. 1, inspection environment 100 may be an example of an environment in which group of standards 102 may be established and used. As used herein, a "group of" items means one or more items. In this manner, group of standards 102 may be one or more standards.

In these illustrative examples, group of standards 102 is configured for use in evaluating any part of selected part type 104. Selected part type 104 may be, for example, without limitation, a type of fastener, a type of spar, a type of rib, a type of panel, a type of skin panel, a type of tube, or some other type of part. A part of selected part type 104 is comprised of composite material 105 in these examples.

Group of standards 102 may be configured for use in evaluating the porosity of any part of selected part type 104 using nondestructive inspection 106. As used herein, "porosity" is a measure of the void spaces within a material. The porosity of a material may be measured as a fraction of the volume of the void spaces within a material over the volume of the material or as a percentage of the volume of the void spaces with respect to the volume of the material.

In these illustrative examples, group of standards 102 is configured for use in evaluating the porosity of a part of selected part type 104, such as, for example, part 108, using nondestructive inspection 106. The porosity of part 108 is referred to as part porosity 110 in these examples. In some cases, group of standards 102 may be referred to as a group of nondestructive inspection porosity standards for part 108.

As depicted, group of standards 102 may be formed from plurality of samples 112. In these illustrative examples, plurality of samples 112 may be formed from section of composite material 113. In particular, section of composite material 113 may be formed having a same set of selected properties as set of selected properties 114 for selected part type 104. Set of selected properties 114 may include, for example, without limitation, at least one of material composition 116, thickness 118, geometry 119, and one or more other types of properties for selected part type 104.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C. In other examples, "at least one of" may be, for example, without limitation, two of item A, one of item B, and ten of item C; four of item B and seven of item C; or some other suitable combination.

In these illustrative examples, section of composite material 113 takes the form of a composite laminate. Section of composite material 113 may be divided into plurality of sections 120 such that the sections in plurality of sections 120 have substantially the same size. Further, each section in plurality of sections 120 may have the same set of selected properties as set of selected properties 114 for selected part type 104.

In these illustrative examples, plurality of techniques 121 may be used to form plurality of samples 112 from plurality of sections 120 such that each sample in plurality of samples 112 has a different porosity from the other samples in plurality of samples 112. In particular, a different technique may be used with each section in plurality of sections 120.

Plurality of techniques 121 may include, for example, without limitation, plurality of curing techniques 122. In particular, a different curing technique from plurality of curing techniques 122 is used to cure each section in plurality of sections 120. Each curing technique in plurality of curing techniques 122 may comprise at least one of a different cure cycle length, a different curing temperature, a different curing pressure, a different curing vacuum, a different curing device, and one or more other different factors.

A number of curing devices may be used to implement plurality of curing techniques 122. As used herein, a "number of" items means one or more items. In this manner, a number of curing devices may be one or more curing devices. The different curing techniques in plurality of curing techniques 122 are selected and implemented such that each sample in plurality of samples 112 formed by curing a corresponding section in plurality of sections 115 has a different porosity from a number of other samples in plurality of samples 112.

As one illustrative example, curing technique 124 may be an example of one of plurality of curing techniques 122 and section 126 may be an example of one of plurality of sections 120. Curing technique 124 may be used to cure section 126 to form sample 128 having porosity 130. Porosity 130 may be different from the porosity of at least one other sample in plurality of samples 112.

Of course, in other illustrative embodiments, one or more other techniques from plurality of techniques 121 may be used with section 126 in addition to and/or in place of curing technique 124 to form sample 128 having porosity 130. For example, without limitation, at least one of curing technique 124, a drying technique, a layup technique, a moisture controlling technique, and some other type of technique may be used to control porosity 130 of sample 128.

Computed tomography (CT) system 132 in inspection environment 100 is used to generate plurality of three-dimensional images 134 for plurality of samples 112. In particular, plurality of three-dimensional images 134 includes a three-dimensional image for each sample in plurality of samples 112.

As one illustrative example, three-dimensional image 136 may be generated for sample 128 using computed tomography system 132. Three-dimensional image 136 comprises plurality of two-dimensional images 138. Each two-dimensional image in plurality of two-dimensional images 138 is a cross-sectional image of sample 128 taken along a single axis of rotation. These cross-sectional images may also be referred to as tomographic sections or tomographic slices.

Plurality of three-dimensional images 134 may be sent to data manager 140 for processing. Data manager 140 may be implemented using hardware, software, or a combination of the two. For example, data manager 140 may be implemented in computer system 142. Computer system 142 may comprise a number of computers. When more than one computer is present in computer system 142, these computers may be in communication with each other.

In some cases, a portion of computer system 142 may be considered part of computed tomography system 132. In other cases, computer system 142 may be located entirely in a location that is remote to computed tomography system 132.

Data manager 140 comprises first data analyzer 144 and second data analyzer 146. First data analyzer 144 receives plurality of three-dimensional images 134 for processing. First data analyzer 144 is configured to extract volumetric data 148 for each sample in plurality of samples 112 using plurality of three-dimensional images 134.

For example, first data analyzer 144 may identify first volume 150 and second volume 152 for sample 128 using three-dimensional image 136. First volume 150 may be the volume of the void spaces within sample 128. Second volume 152 may be the volume of sample 128. First data analyzer 144 uses first volume 150 and second volume 152 to identify porosity 130 of sample 128.

In this manner, first data analyzer 144 identifies plurality of porosity levels 154 for plurality of samples 112. As used herein, a "porosity level" may be a fraction, a percentage, or some other type of measurement of porosity. Plurality of porosity levels 154 identified for plurality of samples 112 based on volumetric data 148 extracted from plurality of three-dimensional images 138 generated by computed tomography system 132 may be have a desired level of accuracy within selected tolerances.

Consequently, the accuracy provided by using computed tomography system 132 may allow smaller sizes of samples to be used for establishing standards as compared to when a computed tomography system is not used. Identifying plurality of porosity levels 154 for plurality of samples 112 may be more easily and quickly performed using volumetric data 148 extracted from plurality of three-dimensional images 134 generated by computed tomography system 132 as compared to when computed tomography system 132 is not used.

First data analyzer 144 compares plurality of porosity levels 154 to group of selected porosity levels 156. Group of selected porosity levels 156 may be the porosity levels for which group of standards 102 is to be established. First data analyzer 144 identifies the samples in plurality of samples 112 having porosity levels that match group of selected porosity levels 156 within selected tolerances.

In particular, for each selected porosity level in group of selected porosity levels 156, first data analyzer 144 identifies the sample in plurality of samples 112 having a porosity level that most closely matches the selected porosity level. In some cases, first data analyzer 144 generates a report identifying the samples in plurality of samples 112 that have porosity levels most closely matching group of selected porosity levels 156. These identified samples form group of standards 102.

In some illustrative examples, group of standards 102 may be established by labeling the identified samples from plurality of samples 112 with the corresponding porosity levels for the samples using labeling system 158. Labeling system 158 may be, for example, without limitation, a marker, a pen, a stamping device, a labeling device, or some other type of labeling system. As one illustrative example, an operator may mark each standard in group of standards 102 with the corresponding selected porosity level from group of selected porosity levels 156 represented by the standard.

Group of standards 102 may be stored in, for example, a storage location, for future use in evaluating any part having the same set of selected properties as set of selected properties 114 for selected part type 104 using nondestructive inspection 106. Further, group of standards 102 may be used multiple times for performing inspections of different parts of selected part type 104 over time.

In one illustrative example, nondestructive inspection system 160 is selected for use in performing nondestructive inspection 106 of part 108. Nondestructive inspection system 160 performs nondestructive inspection 106 of group of standards 102 to generate reference inspection data 162. Further, nondestructive inspection system 160 performs nondestructive inspection 106 of part 108 to generate part inspection data 164. In some cases, part inspection data 164 and reference inspection data 162 may be generated by performing ultrasonic testing using nondestructive inspection system 106 in the form of an ultrasonic testing system.

Reference inspection data 162 and part inspection data 164 may be sent to data manager 140 for processing. Second data analyzer 146 in data manager 140 receives reference inspection data 162 and part inspection data 164. Second data analyzer 146 uses reference inspection data 162 and part inspection data 164 to determine whether part 108 meets selected criteria 166 for part porosity 110. Selected criteria 166 may comprise, for example, without limitation, selected threshold 168.

As one illustrative example, part inspection data 164 may be compared to reference inspection data 162 to determine which standard in group of standards 102 part 108 most closely matches. The selected porosity level corresponding to this standard may be used as part porosity estimate 170 for part 108. If part porosity estimate 170 is greater than selected threshold 168, part 108 may be identified as not meeting selected criteria 166 for part porosity 110. Consequently, part 108 may need to be reworked, replaced, or processed in some other manner.

In this manner, the illustrative embodiments provide a method and apparatus for establishing and using group of standards 102 for use in evaluating the porosity of a part. The method for establishing group of standards 102 for porosity of a part as described above may be performed more quickly, more easily, and more accurately than some currently available methods for establishing standards for porosity.

For example, an entire sample, such as sample 128, may be imaged using computed tomography system 132 and a porosity level for the sample may be identified using the three-dimensional image of the sample generated by computed tomography system 132. In particular, a porosity level may be identified based on volumetric data 148 extracted from the three-dimensional image for the entire sample. This type of identification of porosity for the entire sample may be more accurate as compared to the identification of the porosity for the entire sample based on an estimation of the porosity for an edge of the sample.

Further, the method for establishing group of standards 102 for porosity of a part described above may be less expensive as compared to some currently available methods. For example, once plurality of sections 120 has been formed from section of composite material 113, additional operations other than curing operations may not be needed to form plurality of samples 112.

The illustration of inspection environment 100 in FIG. 1 is not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

In some illustrative examples, first data analyzer 144 may be implemented within computed tomography system 132. In other illustrative examples, second data analyzer 146 may be implemented within nondestructive inspection system 160. In still other illustrative examples, first data analyzer 144 and second data analyzer 146 may form a single data analyzer.

In some cases, plurality of samples 112 may be formed from multiple pieces of composite material instead of section of composite material 113. As one illustrative example, each sample in plurality of samples 112 may be formed from a different section of composite material. Further, any combination of techniques may be used to form, cure, and/or otherwise manipulate plurality of sections 120 such that each sample in plurality of samples 112 has a different porosity from the other samples in plurality of samples 112.

Figure 2:
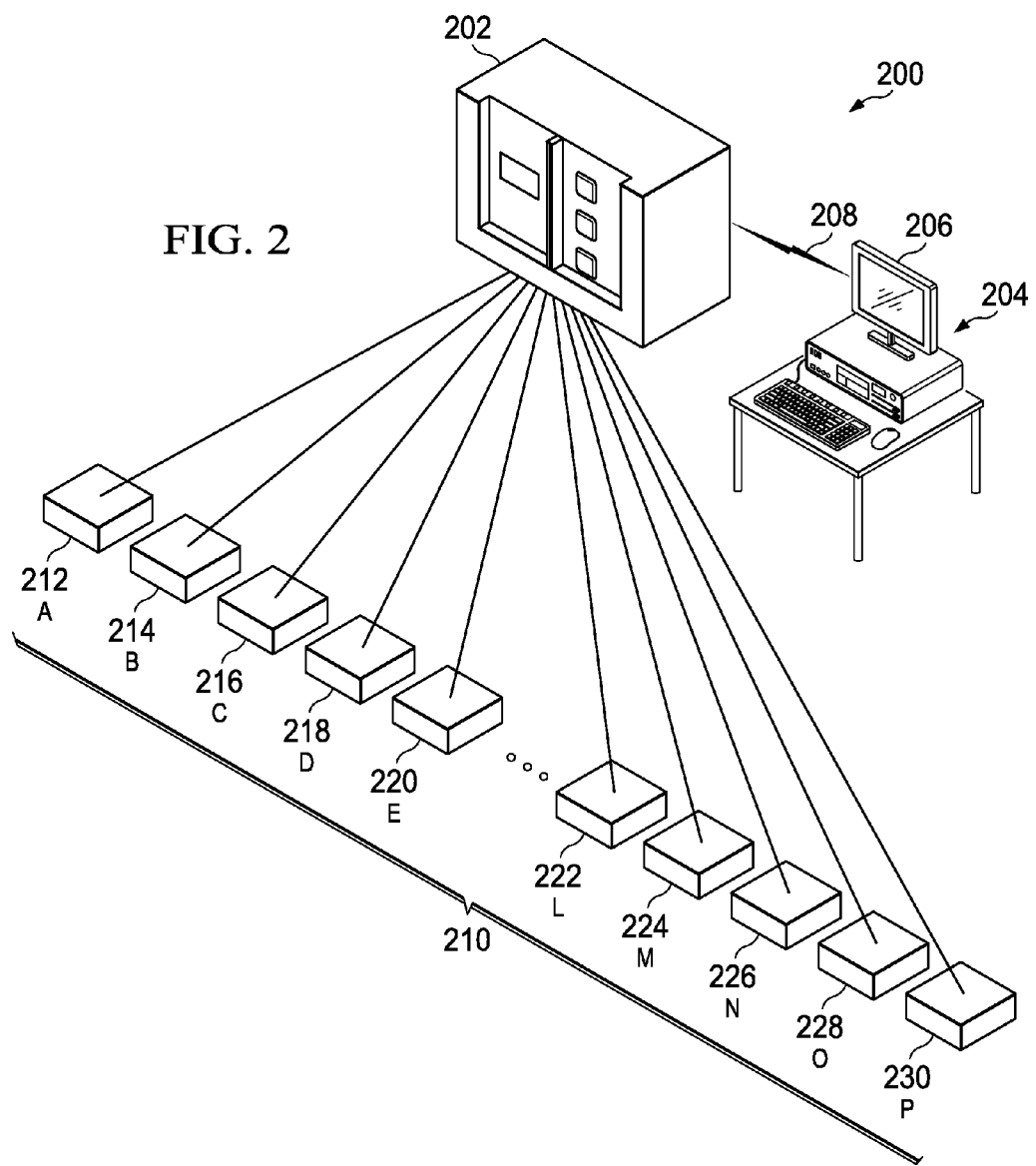
FIG. 2 is an illustration of an inspection environment in accordance with an illustrative embodiment.

With reference now to FIG. 2, an illustration of an inspection environment is depicted in accordance with an illustrative embodiment. In these illustrative examples, inspection environment 200 may be an example of one implementation of inspection environment 100 in FIG. 1. As depicted, inspection environment 200 includes computed tomography system 202 and data manager 204 implemented in computer system 206. Computer system 206 and computed tomography system 202 may be capable of exchanging data over wireless communications link 208.

In this illustrative example, computed tomography system 202 is used to generate three-dimensional images for plurality of samples 210. As depicted, plurality of samples 210 includes sample A 212, sample B 214, sample C 216, sample D 218, sample E 220, sample L 222, sample M 224, sample N 226, sample O 228, and sample P 230. In some cases, plurality of samples 210 may also include additional samples not shown in this figure.

Each of plurality of samples 210 has the same set of selected properties as a selected part type. For example, each sample may have the same material composition and the same thickness as a type of composite skin panel.

The three-dimensional images generated by computed tomography system 202 may be used by, for example, without limitation, first data analyzer 144 in FIG. 1, to identify a porosity level for each of plurality of samples 210. The samples in plurality of samples 210 having porosity levels that most closely match a group of selected porosity levels are selected for establishing a group of standards for porosity.

Figure 3:
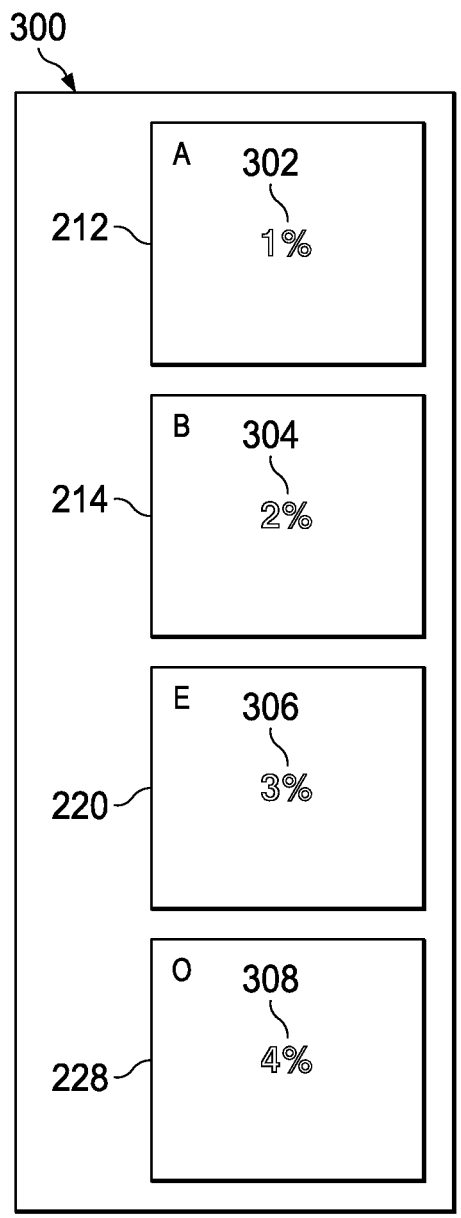
FIG. 3 is an illustration of a group of standards in accordance with an illustrative embodiment.

Turning now to FIG. 3, an illustration of a group of standards is depicted in accordance with an illustrative embodiment. In this illustrative example, group of standards 300 may be an example of one implementation for group of standards 102 in FIG. 1. Group of standards 300 may be used when evaluating a composite skin panel having the same material composition and same thickness as each of group of standards 300 for porosity using a nondestructive inspection system.

As depicted, group of standards 300 has been established using sample A 212, sample B 214, sample E 220, and sample O 228 from plurality of samples 212 in FIG. 2. In particular, sample A 212 has been labeled with selected porosity level 302 establishing sample A 212 as a standard. Sample B 214 has been labeled with selected porosity level 304 establishing sample B 214 as a standard. Further, sample E 220 has been labeled with selected porosity level 306 establishing sample E 220 as a standard. Sample O 228 has been labeled with selected porosity level 308 establishing sample O 228 as a standard.

The illustrations of inspection environment 200 in FIG. 2 and group of standards 300 in FIG. 3 are not meant to imply physical or architectural limitations to the manner in which an illustrative embodiment may be implemented. Other components in addition to or in place of the ones illustrated may be used. Some components may be optional. Further, some of the components in FIGS. 2-3 may be illustrative examples of how components shown in block form in FIG. 1 can be implemented as physical structures. The different components shown in FIGS. 2-3 may be combined with components in FIG. 1, used with components in FIG. 1, or a combination of the two.

Figure 4:
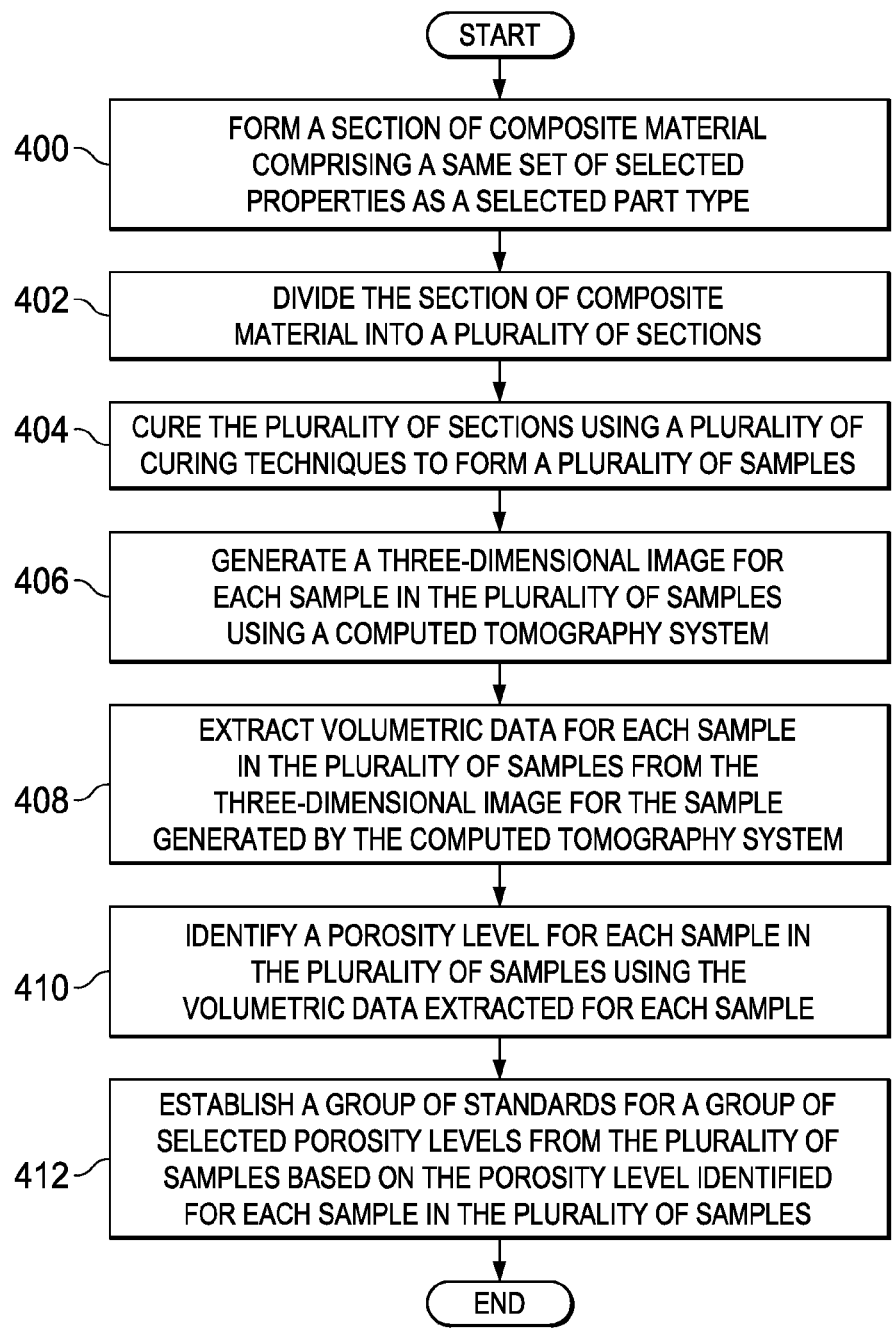
FIG. 4 is an illustration of a process for establishing nondestructive inspection standards in the form of a flowchart in accordance with an illustrative embodiment.

With reference now to FIG. 4, an illustration of a process for establishing nondestructive inspection standards in the form of a flowchart is depicted in accordance with an illustrative embodiment. The process illustrated in FIG. 4 may be implemented to establish a group of standards, such as, for example, without limitation, group of standards 102 in FIG. 1.

The process begins by forming a section of composite material comprising the same set of selected properties as a selected part type (operation 400). The set of selected properties includes at least one of material composition, thickness, and geometry. Next, the process divides the section of composite material into a plurality of sections (operation 402). In these illustrative examples, operation 402 is performed such that each section in the plurality of sections has the same size. Further, each section has the same set of selected properties as the selected part type.

Thereafter, the process cures the plurality of sections using a plurality of curing techniques to form a plurality of samples (operation 404). In this manner, each sample in the plurality of samples has the same set of selected properties as the selected part type. In operation 404, the plurality of samples is formed using a different curing technique from the plurality of curing techniques for each sample in the plurality of samples. Each sample is formed using a different curing technique such that each sample has a different porosity from a number of other samples in the plurality of samples.

The process then generates a three-dimensional image for each sample in the plurality of samples using a computed tomography system (operation 406). In operation 406, a plurality of three-dimensional images are generated. Each three-dimensional image comprises a plurality of two-dimensional images.

Then, the process extracts volumetric data for each sample in the plurality of samples from the three-dimensional image for the sample generated by the computed tomography system (operation 408). Thereafter, a porosity level for each sample in the plurality of samples is identified using the volumetric data extracted for each sample (operation 410). In this manner, a plurality of porosity levels are identified in operation 410.

Next, a group of standards for a group of selected porosity levels is established from the plurality of samples based on the porosity level identified for each sample in the plurality of samples (operation 412), with the process terminating thereafter. In operation 412, the samples having a porosity level that most closely matches a selected porosity level in the group of selected porosity levels is selected for forming a standard. In this manner, a sample is selected for each selected porosity level in group of selected porosity levels.

In some illustrative examples, each standard in the group of standards established in operation 412 is labeled with the selected porosity level corresponding to that standard. Further, the group of standards may be stored for future use in evaluating a part of the selected part type for porosity using a nondestructive inspection system.

Figure 5:
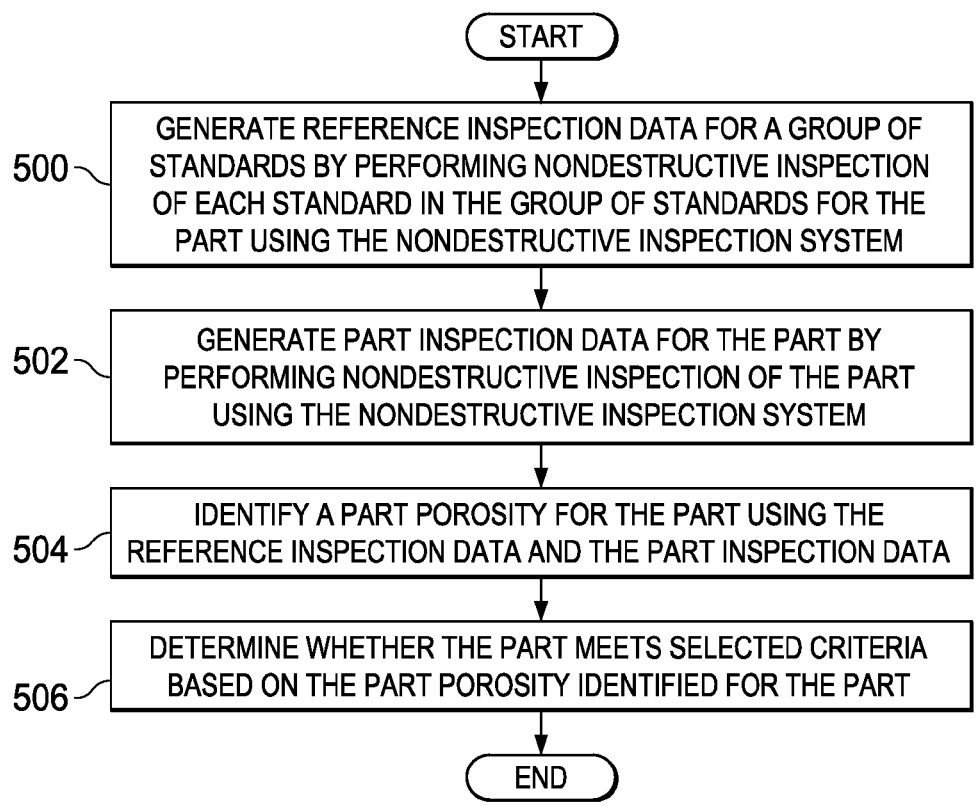
FIG. 5 is an illustration of a process for evaluating a part using a nondestructive inspection system in the form of a flowchart in accordance with an illustrative embodiment.

With reference now to FIG. 5, an illustration of a process for evaluating a part using a nondestructive inspection system in the form of a flowchart is depicted in accordance with an illustrative embodiment. The process illustrated in FIG. 5 may be implemented to evaluate a part, such as part 108 in FIG. 1, using a nondestructive inspection system, such as nondestructive inspection system 160 in FIG. 1.

The process begins by generating reference inspection data for a group of standards by performing nondestructive inspection of each standard in the group of standards for the part using the nondestructive inspection system (operation 500). The group of standards may be, for example, the group of standards established using the process illustrated in FIG. 4.

Next, the process generates part inspection data for the part by performing nondestructive inspection of the part using the nondestructive inspection system (operation 502). Thereafter, the process identifies a part porosity for the part using the reference inspection data and the part inspection data (operation 504). In one illustrative example, the part porosity may be identified by determining which standard the part most closely matches based on the reference inspection data and the part inspection data. The selected porosity level corresponding to this standard may be used as a part porosity estimate for the part porosity of the part.

The process then determines whether the part meets selected criteria based on the part porosity identified for the part (operation 506), with the process terminating thereafter. In one illustrative example, in operation 506, the part porosity identified may be compared to a selected threshold. If the part porosity is greater than the selected threshold, the part is identified as not meeting the selected criteria.

Otherwise, if the part porosity is less than or substantially equal to the selected threshold, the part is identified as meeting the selected criteria.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram Turning now to FIG. 6, an illustration of a data processing system in the form of a block diagram is depicted in accordance with an illustrative embodiment. In this illustrative example, data processing system 600 may be used to implement one or more computers in computer system 142 in FIG. 1. In this illustrative example, data processing system 600 includes communications framework 602, which provides communications between processor unit 604, memory 606, persistent storage 608, communications unit 610, input/output (I/O) unit 612, and display 614.

Processor unit 604 serves to execute instructions for software that may be loaded into memory 606. Processor unit 604 may be a number of processors, a multi-processor core, or some other type of processor, depending on the particular implementation. "A number of", as used herein with reference to an item, means one or more items. Further, processor unit 604 may be implemented using a number of heterogeneous processor systems in which a main processor is present with secondary processors on a single chip. As another illustrative example, processor unit 604 may be a symmetric multi-processor system containing multiple processors of the same type.

Memory 606 and persistent storage 608 are examples of storage devices 616. A storage device is any piece of hardware that is capable of storing information, such as, for example, without limitation, data, program code in functional form, and/or other suitable information either on a temporary basis and/or a permanent basis. Storage devices 616 also may be referred to as computer readable storage devices or non-transitory storage devices in these examples. Memory 606, in these examples, may be, for example, a random access memory or any other suitable volatile or non-volatile storage device. Persistent storage 608 may take various forms, depending on the particular implementation.

For example, persistent storage 608 may contain one or more components or devices. For example, persistent storage 608 may be a hard drive, a flash memory, a rewritable optical disk, a rewritable magnetic tape, or some combination of the above. The media used by persistent storage 608 also may be removable. For example, a removable hard drive may be used for persistent storage 608.

Communications unit 610, in these examples, provides for communications with other data processing systems or devices. In these examples, communications unit 610 is a network interface card. Communications unit 610 may provide communications through the use of either or both physical and wireless communications links.

Input/output unit 612 allows for input and output of data with other devices that may be connected to data processing system 600. For example, input/output unit 612 may provide a connection for user input through a keyboard, a mouse, and/or some other suitable input device. Further, input/output unit 612 may send output to a printer. Display 614 provides a mechanism to display information to a user.

Instructions for the operating system, applications, and/or programs may be located in storage devices 616, which are in communication with the processor unit 604 through communications framework 602. In these illustrative examples, the instructions are in a functional form on persistent storage 608. These instructions may be loaded into memory 606 for execution by processor unit 604. The processes of the different embodiments may be performed by processor unit 604 using computer-implemented instructions, which may be located in a memory, such as memory 606.

These instructions are referred to as program code, computer usable program code, or computer readable program code that may be read and executed by a processor in processor unit 604. The program code in the different embodiments may be embodied on different physical or computer readable storage media, such as memory 606 or persistent storage 608.

Program code 618 is located in a functional form on computer readable media 620 that is selectively removable and may be loaded onto or transferred to data processing system 600 for execution by processor unit 604. Program code 618 and computer readable media 620 form computer program product 622 in these examples. In one example, computer readable media 620 may be computer readable storage media 624 or computer readable signal media 626.

Computer readable storage media 624 may include, for example, an optical or magnetic disk that is inserted or placed into a drive or other device that is part of persistent storage 608 for transfer onto a storage device, such as a hard drive, that is part of persistent storage 608. Computer readable storage media 624 also may take the form of a persistent storage, such as a hard drive, a thumb drive, or a flash memory, that is connected to data processing system 600. In some instances, computer readable storage media 624 may not be removable from data processing system 600.

In these examples, computer readable storage media 624 is a physical or tangible storage device used to store program code 618 rather than a medium that propagates or transmits program code 618. Computer readable storage media 624 is also referred to as a computer readable tangible storage device or a computer readable physical storage device. In other words, computer readable storage media 624 is a media that can be touched by a person.

Alternatively, program code 618 may be transferred to data processing system 600 using computer readable signal media 626. Computer readable signal media 626 may be, for example, a propagated data signal containing program code 618. For example, computer readable signal media 626 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 618 may be downloaded over a network to persistent storage 608 from another device or data processing system through computer readable signal media 626 for use within data processing system 600. For instance, program code stored in a computer readable storage medium in a server data processing system may be downloaded over a network from the server to data processing system 600. The data processing system providing program code 618 may be a server computer, a client computer, or some other device capable of storing and transmitting program code 618.

The different components illustrated for data processing system 600 are not meant to provide architectural limitations to the manner in which different embodiments may be implemented. The different illustrative embodiments may be implemented in a data processing system including components in addition to or in place of those illustrated for data processing system 600. Other components shown in FIG. 6 can be varied from the illustrative examples shown. The different embodiments may be implemented using any hardware device or system capable of running program code. As one example, the data processing system may include organic components integrated with inorganic components and/or may be comprised entirely of organic components excluding a human being. For example, a storage device may be comprised of an organic semiconductor.

In another illustrative example, processor unit 604 may take the form of a hardware unit that has circuits that are manufactured or configured for a particular use. This type of hardware may perform operations without needing program code to be loaded into a memory from a storage device to be configured to perform the operations.

For example, when processor unit 604 takes the form of a hardware unit, processor unit 604 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a field programmable logic array, a field programmable gate array, and other suitable hardware devices. With this type of implementation, program code 618 may be omitted, because the processes for the different embodiments are implemented in a hardware unit.

In still another illustrative example, processor unit 604 may be implemented using a combination of processors found in computers and hardware units. Processor unit 604 may have a number of hardware units and a number of processors that are configured to run program code 618. With this depicted example, some of the processes may be implemented in the number of hardware units, while other processes may be implemented in the number of processors.

In another example, a bus system may be used to implement communications framework 602 and may be comprised of one or more buses, such as a system bus or an input/output bus. Of course, the bus system may be implemented using any suitable type of architecture that provides for a transfer of data between different components or devices attached to the bus system.

Additionally, a communications unit may include a number of devices that transmit data, receive data, or transmit and receive data. A communications unit may be, for example, a modem or a network adapter, two network adapters, or some combination thereof. Further, a memory may be, for example, memory 606 or a cache, such as found in an interface and memory controller hub that may be present in communications framework 602.

Thus, the illustrative embodiments provide a method and apparatus for establishing nondestructive inspection standards. In one illustrative embodiment, a method for establishing nondestructive inspection standards is provided. A plurality of samples is formed using a different curing technique for each sample in the plurality of samples such that each sample in the plurality of samples has a different porosity from a number of other samples in the plurality of samples. Each sample in the plurality of samples has a same set of selected properties as a selected part type. A porosity level is identified for each sample in the plurality of samples using volumetric data extracted from a three-dimensional image for each sample generated using a computed tomography system. A group of standards is established for a group of selected porosity levels from the plurality of samples based on the porosity level identified for each sample in the plurality of samples. The group of standards is configured for use in performing nondestructive inspection of a part of the selected part type.

Additionally, in another illustrative embodiment, a method for evaluating a part using a nondestructive inspection system is provided. Reference inspection data is generated for a group of standards by performing nondestructive inspection of each standard in the group of standards for the part using the nondestructive inspection system. The group of standards is established from a plurality of samples based on a porosity identified for each sample in the plurality of samples using volumetric data extracted from a three-dimensional image for each sample generated using a computed tomography system. Part inspection data is generated for the part by performing nondestructive inspection of the part using the nondestructive inspection system. A porosity is identified for the part using the reference inspection data and the part inspection data.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for establishing nondestructive inspection standards, the method comprising:
    forming a plurality of samples using a different technique for each sample in the plurality of samples such that the each sample in the plurality of samples has a different porosity from a number of other samples in the plurality of samples, wherein the each sample in the plurality of samples has a same set of selected properties as a selected part type;
    identifying a porosity level for the each sample in the plurality of samples using volumetric data extracted from a three-dimensional image for the each sample generated using a computed tomography system; and
    establishing a group of standards for a group of selected porosity levels from the plurality of samples based on the porosity level identified for the each sample in the plurality of samples, wherein the group of standards is configured for use in performing nondestructive inspection of a part of the selected part type, wherein establishing the group of standards includes: identifying the group of selected porosity levels for use in evaluating the selected part type, and establishing a sample in the plurality of samples having the porosity level that matches a selected porosity level in the group of selected porosity levels within selected tolerances as a standard in the group of standards.

2. The method of claim 1 further comprising:
    generating the three-dimensional image for the each sample in the plurality of samples using the computed tomography system, wherein the three-dimensional image comprises a plurality of two-dimensional images.

3. The method of claim 1, wherein the step of identifying the porosity level for the each sample in the plurality of samples using the volumetric data extracted from the three-dimensional image for the each sample generated using the computed tomography system comprises:
    extracting the volumetric data for the each sample in the plurality of samples from the three-dimensional image for the each sample generated by the computed tomography system;
    identifying a first volume for void spaces within the each sample;
    identifying a second volume of the each sample; and
    identifying the porosity level for the each sample in the plurality of samples using the first volume for the void spaces within the each sample and the second volume of the each sample.

4. The method of claim 1, wherein the step of forming the plurality of samples using the different technique for the each sample in the plurality of samples comprises:
    curing a sample in the plurality of samples with a curing technique selected from a plurality of curing techniques, wherein each curing technique in the plurality of curing techniques comprises at least one of a different cure cycle length, a different curing temperature, a different curing pressure, a different curing vacuum, and a different curing device.

5. The method of claim 1, wherein the step of forming the plurality of samples using the different technique for the each sample in the plurality of samples comprises:
    forming a section of composite material comprising the same set of selected properties as the selected part type, wherein the same set of selected properties includes at least one of material composition, thickness, and geometry; and
    dividing the section of composite material into a plurality of sections in which each section in the plurality of sections has a same size.

6. The method of claim 5, wherein the step of forming the plurality of samples using the different curing technique for the each sample in the plurality of samples further comprises:
    curing the plurality of sections using a plurality of curing techniques to form the plurality of samples.

7. The method of claim 1 further comprising:
    storing the group of standards for future use in evaluating any part having the same set of selected properties as the selected part type, wherein the set of selected properties comprises at least one of material composition, thickness, and geometry.

8. A method for evaluating a part using a nondestructive inspection system, the method comprising:
    generating reference inspection data for a group of standards by performing nondestructive inspection of each standard in the group of standards for the part using the nondestructive inspection system;
    wherein the group of standards is established from a plurality of samples based on a porosity level identified for each sample in the plurality of samples using volumetric data extracted from a three-dimensional image for the each sample generated using a computed tomography system, wherein establishing the group of standards includes: identifying the group of selected porosity levels for use in evaluating the selected part type, and establishing a sample in the plurality of samples having the porosity level that matches a selected porosity level in the group of selected porosity levels within selected tolerances as a standard in the group of standards;

generating part inspection data for the part by performing the nondestructive inspection of the part using the nondestructive inspection system; and identifying a part porosity for the part using the reference inspection data and the part inspection data.

9. The method of claim 8, wherein the step of identifying the part porosity for the part using the reference inspection data and the part inspection data comprises:

determining whether the part porosity is greater than a selected threshold using the reference inspection data and the part inspection data.

10. The method of claim 8, wherein the step of generating the reference inspection data for the group of standards by performing the nondestructive inspection of the each standard in the group of standards for the part using the nondestructive inspection system comprises:

generating the reference inspection data for the group of standards by performing ultrasonic testing of the each standard in the group of standards for the part using an ultrasonic testing system.

11. The method of claim 8, wherein the step of generating the part inspection data for the part by performing the nondestructive inspection of the part using the nondestructive inspection system comprises:

generating the part inspection data for the part by performing ultrasonic testing of the part using an ultrasonic testing system.

12. The method of claim 8 further comprising:

storing the group of standards in a storage location for future use in evaluating another part of a same selected part type as the part, wherein the another part has a same set of selected properties as the part in which the same set of selected properties comprises at least one of material composition, thickness, and geometry.

13. An apparatus comprising:

a plurality of samples formed such that each sample in the plurality of samples has a different porosity from a number of other samples in the plurality of samples and such that the each sample in the plurality of samples has a same set of selected properties as a selected part type; and a data analyzer configured to identify a porosity level for the each sample in the plurality of samples using volumetric data extracted from a three-dimensional image for the each sample generated using a computed tomography system, wherein a group of standards for a group of selected porosity levels is established from the plurality of samples based on the porosity level identified for the each sample in the plurality of samples and wherein the group of standards is configured for use in performing nondestructive inspection of a part of the selected part type, wherein the data analyzer is further configured to generate a report identifying a sample in the plurality of samples having the porosity level that matches a selected porosity level in the group of selected porosity levels within selected tolerances.

14. The apparatus of claim 13 further comprising:

the computed tomography system, wherein the computed tomography system is configured to generate the three-dimensional image for the each sample in the plurality of samples in which the three-dimensional image comprises a plurality of two-dimensional images.

15. The apparatus of claim 13, wherein the data analyzer is configured to identify the porosity level for the each sample in the plurality of samples by extracting the volumetric data for the each sample in the plurality of samples from the three-dimensional image for the each sample generated by the computed tomography system; identify a first volume for void spaces within the each sample; identify a second volume of the each sample; and identify the porosity level for the each sample in the plurality of samples using the first volume for the void spaces within the each sample and the second volume of the each sample.

16. The apparatus of claim 13 further comprising:

a labeling system, wherein each standard in the group of standards is configured to be labeled with a corresponding selected porosity level for the each standard in the group of selected porosity levels.

17. The apparatus of claim 13 further comprising:

a number of curing devices, wherein the each sample in the plurality of samples is cured using at least one curing device in the number of curing devices and a curing technique selected from a plurality of curing techniques, wherein each curing technique in the plurality of curing techniques comprises at least one of a different cure cycle length, a different curing temperature, a different curing pressure, a different curing vacuum, and a different curing device.

18. The apparatus of claim 13, wherein the same set of selected properties includes at least one of material composition, thickness, and geometry and wherein the each sample in the plurality of samples is comprised of a same composite material as the part of the selected part type.

\* \* \* \* \*